United States Patent [19]

Kaufman

[11] 4,298,614
[45] Nov. 3, 1981

[54] 5′-AMINOALKYL-4′,4-DIALKYLPSORALENS

[75] Inventor: Kurt D. Kaufman, Kalamazoo, Mich.

[73] Assignee: Thomas C. Elder, Inc., Hamilton, Ind.

[21] Appl. No.: 73,908

[22] Filed: Sep. 10, 1979

[51] Int. Cl.³ ............... C07D 493/04; A61K 31/365
[52] U.S. Cl. .......................... 424/279; 260/343.21; 424/59
[58] Field of Search ............... 260/343.21; 424/279, 424/59

[56] References Cited

U.S. PATENT DOCUMENTS 4,124,598  11/1978  Hearst et al. ............ 260/343.21
4,130,568  12/1978  Confalne et al. ......... 260/343.21
4,169,204   9/1979  Heart et al. ............. 260/343.21

OTHER PUBLICATIONS

Dawber, J. Soc. Cosmet. Chem. 28, 403–406, 1977.
Hearst et al., (III) Chem. Abst. 87:78962f.
Martins et al., Chem. Abst. vol. 81, 1974, 99676g.
Chem. Abst. 88:59494j.
Johnston et al., Chem. Abst. 87:147284a.
Isaacs et al., Chem. Abst. 86:135108n.

Primary Examiner—Henry R. Jiles
Assistant Examiner—Jane T. Fan
Attorney, Agent, or Firm—Gordon W. Hueschen

[57] ABSTRACT

The invention relates to 5′-aminoalkyl-4′,4-dialkylpsoralens having enhanced photosensitizing activity, especially oral activity, including early onset, increased maximum, and rapid decline, as well as low toxicity, when compared with psoralens of different structure.

6 Claims, No Drawings

5'-AMINOALKYL-4',4-DIALKYLPSORALENS

BACKGROUND OF THE INVENTION

1. Field of Invention

Psoralens, photochemotherapy, psoralens having enhanced photosensitizing activity for use in photochemotherapy.

2. Prior Art

Psoralens have been used for years as dermalphotosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in a Psoralite (TM) apparatus. A high percentage of remissions of this disease have been effected in such manner.

The effectiveness of a psoralen for such uses and for such purpose is related to its ability to produce erythema upon the skin upon irradiation. Psoralens also have other uses, and their uses, as well as underlying rationale and theory, are partially elucidated in U.S. Pat. No. 4,124,598, and are otherwise well-known in the art from various preexisting publications.

With the increasing emphasis on photochemotherapeutic treatments for various purposes using psoralens and controlled application of ultraviolet light, the requirements for optimally-effective photosensitizing psoralens have become more apparent. To eliminate the necessity of excessive and perhaps dangerous ultraviolet light applications or dosages, maximum photosensitization is one obvious criterion. However, to eliminate excessive periods of waiting before photochemotherapy can be commenced, rapid onset of photosensitization upon topical or oral administration of the photosensitizing agent is also of significance. Perhaps an even more important criterion is rapid decline in photosensitizing activity of the photosensitizing agent after reaching maximum and/or effective photosensitization levels after administration. Obviously, if the photosensitization effect does not decline relatively rapidly, or at least within a reasonably limited period after maximization, a patient must be confined for uneconomic and undesirable periods after treatment so that photosensitization does not continue after the desired ultraviolet light treatment period, with the distinct danger of excessive and undesirable continuance of photochemotherapy because of exposure to normally-encountered light rays upon leaving the treatment area. Thus, the criteria of rapid onset, early maximization, and rapid decline of photosensitization effect have already become established as desirable criteria for the photosensitizing agents in this relatively new but rapidly-expanding field of photochemotherapy, certainly of equal importance as contrasted to the single previously-important criterion of high maximum photosensitization activity alone.

Although some psoralens, such as trimethylpsoralen (4,5',8-trimethylpsoralen or trioxsalen) are characterized by considerable topical activity, they have a diminished order of oral activity, or at least the oral activity is a modicum for purposes of practical photochemotherapeutic utilization. In contrast, 8-methoxypsoralen is characterized by significant oral activity. The psoralen compounds of U.S. Pat. Nos. 4,124,598 and 4,130,568 are also characterized structurally by the presence of an 8 carbon atom substituent, e.g., an 8-methoxy or 8-methyl substituent, which has heretofore apparently been considered desirable for substantial photosensitizing activity, whether oral or topical, of course along with other substituents present in the 4',4, and 5' positions, in those prior art psoralen compounds which have heretofore been found to have desired photochemotherapeutic activity.

OBJECTS OF THE INVENTION

It is an object of the invention to provide novel psoralen compounds. It is a further object to provide novel psoralen compounds which have enhanced characteristics when compared with psoralen compounds of different structure. It is an additional object to provide novel psoralen compounds having enhanced photosensitizing characteristics in accord with the foregoing stated criteria. It is a still further object to provide novel psoralen compounds having enhanced photosensitizing characteristics and relatively low toxicity, and of a structure differing essentially from known psoralen compounds, the advantageous properties of which could not be predicted on a basis of any known structure-activity relationships. Still other objects will be apparent to one skilled in the art and still additional objects will become apparent hereinafter from the following description and claims.

SUMMARY OF THE INVENTION

The present invention relates to 5'-aminoalkyl-4',4-dialkylpsoralens having enhanced photosensitizing activity, especially oral activity, including early onset, increased maximum, and rapid decline, as well as low toxicity, when compared with psoralens of different structure. It is particularly concerned with 5'-primaryaminoloweralkyl-4',4-diloweralkylpsoralens and especially 5'-aminomethyl-4,4'-dimethylpsoralen. It is to be noted that the compounds of this invention have no necessary 8 carbon atom substituent as in the prior art compounds trisoralen (4,5',8-trimethylpsoralen), 8-methoxypsoralen, or the compounds of U.S. Pat. Nos. 4,124,598 and 4,130,568. The compounds are nevertheless characterized by excellent photosensitization activity according to the aforesaid various criteria, as well as relatively low toxicity.

The compounds of the invention have the formula

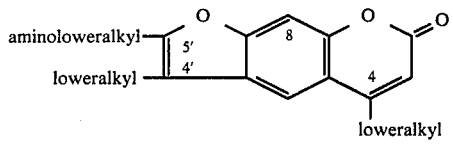

5'-primaryaminoloweralkyl-4'-loweralkyl-4-loweralkylpsoralen, wherein loweralkyl is preferably methyl.

DETAILED DESCRIPTION OF THE INVENTION

The following Preparations and Examples are given by way of illustration only and are not to be construed as limiting.

Appropriate starting umbelliferones (4-alkyl-7-hydroxycoumarins) are known compounds and can be prepared in known manner and converted to psoralens by known procedure (MacLeod and Worth, Tetrahedron Lett., 237–240 (1972)). Variations in the 4-alkyl substituent and in the alkylhalomethyl ketone reactants produce variations in the alkyl group at positions 4,4' of the resulting psoralen as will appear more fully hereinafter, especially from the Examples which follow. Chloroalkylation with a selected chloroalkyl methyl ether introduces a desired chloroalkyl group into the 5' position of the 4',4-dialkylpsoralen nucleus, whereafter reaction with potassium phthalimide followed by cleavage with hydrazine acetate yields the desired 5'-aminoalkyl-4',4-dialkylpsoralen, in which the various alkyl groups correspond to those in the starting 4-alkyl-7-hydroxycoumarin, the alkylhalomethylketone, and the chloroalkylating agent employed. Alternatively, the haloalkylation may be effected according to Olah and Kuhn, J. Org. Chem. 29, 2317 (1964) or Friedel-Crafts and Related Reactions, Vol. II, Part 2, G. A. Olah, ed., Interscience, New York, N.Y., 1964, page 749. The structure of the final 5'-aminoalkyl-4',4-dialkylpsoralen is confirmed by nuclear magnetic resonance spectra, using a Perkin Elmer Model R-24B.

5'-AMINOMETHYL-4',4-DIMETHYLPSORALEN

7-Acetonyloxy-4-methylcoumarin

A mixture of chloroacetone (26.23 mL, 30.48 g, 0.329 mol), potassium iodide (1.0 g, 6 mmol), and reagent grade acetone (dried over $K_2CO_3$, ca. 400 mL) was allowed to stand for $15\frac{1}{2}$ hours. 7-Hydroxy-4-methylcoumarin (50.0 g, 0.284 mol), anhyd. $K_2CO_3$ (45.50 g, 0.321 mol) were added and the mixture was refluxed for 24 hours with overhead stirring. The hot mixture was filtered and the precipitate was washed with acetone. The washes and the filtrate were combined and evaporated in vacuo to obtain a yellow solid, which dissolved in $CHCl_3$ (1.3 L). The $CHCl_3$ solution was extracted once with 5% aq. NaOH (500 mL), washed with two portions (500 mL) of water, dried ($MgSO_4$), and evaporated in vacuo to obtain 7-acetonyloxy-4-methylcoumarin (64.30 g, 97.5%), mp 146.0°–148.0° C. Recrystallization of 61.82 g from 95% ethanol gave a purer product (53.91 g, 87% recovery, 85% yield), mp 150.1°–151.2° C.

4',4-Dimethylpsoralen

A stirred (overhead) mixture of 7-acetonyloxy-4-methylcoumarin (53.48 g, 0.23 mol) and 0.1 N aq. potassium hydroxide (3.69 L, 0.369 mol) was heated gently under reflux for $1\frac{3}{4}$ hours. After cooling to room temperature, the mixture was acidified with 1.0 N aq. HCl and a light yellow precipitate was collected by vacuum filtration, washed with water, and dissolved in $CHCl_3$ (ca. 1.5 L). The $CHCl_3$ solution was washed with three portions (500 mL) of saturated aq. $NaHCO_3$, then with two portions (500 mL) of $H_2O$, dried ($MgSO_4$), and evaporated in vacuo to obtain crude 4',4-dimethylpsoralen (43.41 g, 88%), mp 215°–220° C. Recrystallization from 2-butanone gave the pure product (81% recovery, 71% yield), mp 222.0°–223.5° C. (cf. lit. 220° C.). NMR ($CDCl_3$) $\delta2.3$ (d, 3, J≃1 Hz, 4'-$CH_3$), 2.5 (d, 3, J≃1 Hz, 4-$CH_3$), 6.2 (d, 1, J≃1 Hz, $C_3H$), 7.35 (s, 1, $C_8H$), 7.4 (d, 1, J≃1 Hz, $C_5'H$), 7.6 (s, 1, $C_5H$).

5'-Chloromethyl-4',4 dimethylpsoralen

Chloromethyl methyl ether (242 mL, 3.186 mol) was added to a solution of 4',4-dimethylpsoralen (crude, 30.0 g, 0.14 mol) in glacial acetic acid (3.1 L) and the solution was allowed to stir at room temperature for 48 hours. A second portion of chloromethyl methyl ether (242 mL, 3.186 mol) was added and, after stirring for an additional 48 hours, the solution was poured into water (7.75 L). A white solid was collected by slow filtration, washed with water, and dried in vacuo to give 5'-chloromethyl-4',4-dimethylpsoralen (20.4 g, 55%), mp 159.0°–163.3° C. That material could be recrystallized from benzene with poor recovery, but the product was still not completely pure. Repetition of this process up to the recrystallization step gave a material melting above 270° C. Sublimation (160° C., 0.500 mm) of that material gave pure 5'-chloromethyl-4',4-dimethyl-psoralen, mp 170°–170.2° C. NMR ($CDCl_3$) $\delta2.3$ (s, 3, 4'-$CH_3$), 2.5 (br s, 3, 4-$CH_3$), 4.7 (s, 2, $CH_2Cl$), 6.2 (br s, 1, $C_3H$), 7.3 (s, 1, $C_8H$), 7.6 (s, 1, $C_5H$).

Anal. Calcd. for $C_{14}H_{11}O_3Cl$: C, 64.01; H, 4.22; Cl, 13.50. Found: C, 63.80; H, 4.24; Cl, 12.49.

4',4-Dimethyl-5'-phthalimidomethylpsoralen

Potassium phthalimide (0.275 g, 1.39 mmol) was added to a solution of 5'-chloro-methyl-4',4-dimethylpsoralen (0.304 g, 1.16 mmol) in dry (molecular sieves) DMF (31 mL) at room temperature. The mixture was heated at 100° C. with stirring for six hours, while being protected from atmospheric moisture, and then was poured into ice water (100 mL). A tan solid was collected by suction filtration, washed with two portions (100 mL) of water, and dried in vacuo to obtain 5'-phthalimidomethyl-4',4-dimethylpsoralen (0.368 g, 85%) mp(G) 302°–312° C. It crystallizes from glacial acetic acid but an analytical sample, mp(G) 316°–320° C., was obtained by vacuum sublimation. Anal. Calcd. for $C_{22}H_{15}O_5N$: C, 70.77; H, 4.05; N, 3.75. Found: C, 70.50; H, 4.11; N, 3.63.

5'-Aminomethyl-4',4-dimethylpsoralen

A solution of 4',4-dimethyl-5'-phthalimidomethylpsoralen (6.4 g, 17 mmol) and 85% hydrazine hydrate (7.8 mL, 137 mmol) in 95% ethanol (1536 mL) was heated under reflux for 6 hours, and evaporated in vacuo to obtain an off-white solid. Addition of 0.1 N NaOH (500 mL), followed by extraction with three portions (500 mL) of $CHCl_3$, drying ($Na_2SO_4$), and evaporation of the $CHCl_3$ extracts in vacuo, gave 5'-aminomethyl-4',4-dimethylpsoralen (3.3 g, 80.5%), mp 180.2°–183° C. Recrystallization from a benzene-ligroin (bp 94°–105° C.) solvent pair gave two crops: 2.437 g (59%), mp 183.2°–184.5° C.; and 0.433 g (11%), mp 181.7°–184° C. (NMR ($CDCl_3$) $\delta1.6$ (s, 2, $NH_2$, exchangable with $D_2O$), 2.2 (s, 3, 4'-$CH_3$), 2.4 (d, 3, J≃1 Hz, 4-$CH_3$), 3.9 (s, 2, $CH_2$), 6.1 (d, 1, J≃1 Hz, $C_3H$), 7.2 (s, 1, $CH_8H$), 7.45 (s, 1, $C_5H$).

Anal. Calcd. for $C_{14}H_{13}O_3N$: C, 69.12; H, 5.39; N, 5.76. Found: C, 68.83; H, 5.50; N, 5.50.

5'-Aminoethyl-4'-ethyl-4-methylpsoralen

In the same manner as given in the foregoing, but using ethylchloromethyl ketone and chloroethyl methyl ether in Steps 1 and 3, respectively, in place of chloroacetone and chloromethyl methyl ether, the title compound is produced.

5'-Aminomethyl-4'-propyl-4-methylpsoralen

In the same manner as given in the foregoing, but using propylchloromethyl ketone in Step 1 instead of chloroacetone, the title compound is produced.

5'-Aminomethyl-4'-methyl-4-ethylpsoralen

In the same manner as given in the foregoing, but starting from 7-hydroxy-4-ethylcoumarin instead of 7-hydroxy-4-methylcoumarin in Step 1, the title compound is produced.

In the same manner as given in the foregoing, other variations in selection of starting materials are productive of still other 5'-aminoloweralkyl-4',4-diloweralkylpsoralens within the scope of the invention in which one, two, or all of the loweralkyl groups present in the compound are varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like.

The 5'-aminomethyl-4'-methylpsoralen was made in the same manner, starting from 7-hydroxycoumarin, for comparison purposed. The final step of its preparation follows:

A mixture of 4'-methyl-5'-phthalimidomethylpsoralen (6.0 g; 16.7 mmol), absolute ethanol (1.2 L, not dried), glacial acetic acid (15.24 mL, 266 mmol), and 85% hydrazine hydrate (7.63 mL 113 mmol) was heated under reflux for six hours and concentrated in vacuo to an off-white solid. HCl (1 F, 500 mL) was added, followed by $NaHCO_3$(s) until the pH was ca. 8.0, and the mixture was extracted with three portions (500 mL) of $CHCl_3$, which were dried ($Na_2SO_4$), and concentrated in vacuo to obtain 5'-aminomethyl-4'-methylpsoralen (2.945 g, 77%), mp 153.1°–156.3° C. Recrystallization from a benzene-ligroin (bp 94°–105°) solvent pair gave an analytical sample (73% recovery), mp 154.1°–156.1° C. NMR ($CDCl_3$) $\delta$1.7 (br s, 2, $NH_2$, exchangable with $D_2O$), 2.25 (s, 3, 4'-$CH_3$), 3.95 (s, 2, $CH_2$), 6.31 (d, 1, J=9 Hz, $C_3H$), 7.32 (s, 1, $C_8H$), 7.46 (s, 1, $C_5H$), 7.75 (d, 1, J=9 Hz, $C_4H$).

Anal. Calcd. for $C_{13}H_{11}O_3N$: C, 68.11; H, 4.84; N, 6.11. Found: C, 67.94; H, 4.85; N, 5.82.

PHARMACOLOGY

The biophotosensitization activity of the compounds of the present invention was determined by visual grading of erythemal response according to a modification of the procedure of Pathak and Fitzpatrick, J. Invest. Dermatol. 32, 509–518 (1959), entitled "Bioassay of Natural and Synthetic Furocoumarins (Psoralens)". (The psoralens are of course "linear" isomers of the furocoumarin family.) According to this bioassay of photosensitizing potency, erythema production of albino guinea pig skin is measured visually and the response accorded a gradation definition according to a 0, $\mp$, 1, 2, 3, and 4 scale. The modification employed involved variation of the time between administration of the test compound and exposure to ultraviolet light, thereby enabling measurement of times of onset and decline of the induced photosensitivity effect.

PROTOCOLS

Topical: Each drug is tested topically at a concentration of one percent (1%) in ethanolic solution. Test sites of one square centimeter of skin each receive one-tenth milliliter of a particular selected test solution thirty minutes prior to exposure to three joules of ultraviolet "A" radiation. Three species of fifteen in each group of guinea pigs are tested with each product to arrive at an average response designated "Reaction Intensity", which is determined by observation and grading 24 hours and 48 hours after administration.

Oral: Each drug is tested orally by administering a dosage of forty (40) mgm/kgm of body weight to groups of fifteen guinea pigs. The appropriate dosage for each animal is packed into a gelatin capsule and placed far back in the animal's pharynx. Swallowing is assisted by syringe delivery of three milliliters of water. The animals are not allowed to eat or drink six hours before and after administration of each product. The exposure to ultraviolet "A" radiation is at a dose of four joules per square centimeter at different times after administration, e.g., 10, 20, 30, 45, 60, 90, 120, 180, 240 minutes after administration. Readings and evaluations are carried out 48 hours post ingestion. When a particular product is exceptionally active in the test, the per os dosage may of course be halved or otherwise reduced.

Gradation: Responses are graded as follows:

0 No response; $\pm$ faint erythema; 1+ erythema; 2+ erythema and slight edema; 3+ erythema and intense edema; and 4+ vesiculobullous reaction.

RESULTS

The compounds of the invention show erythematic topical activity as read at both 24 and 48 hours. They show oral activity as read at 48 hours which is outstanding, with high maxima, early onset, and rapid decline in photosensitizing effect. The compound 5'-aminomethyl-4',4-dimethylpsoralen is particularly outstanding, dropping off to no response or only faint erythema at 240 minutes, with an early onset of vesicubullous reaction at only 20 minutes, maintaining such a maximum through 120 minutes and dropping off to gradation 3+ at 180 minutes. It is superior in photosensitizing maximum and in onset to maximum when compared with 4'-aminomethyl-4,5',8-trimethylpsoralen, and in all respects superior to the control methoxsalen (8-methoxypsoralen) which moreover does not show a rapid decline, exhibiting a 2+ rating after 240 minutes. Its photosensitizing efficiency is still superior in all respects to the halved oral dosage of 20 mgm/kgm. In contrast, the 5'-aminomethyl-4'-methylpsoralen (made by identical procedure from 7-hydroxycoumarin) shows essentially no photosensitizing response orally, although it exhibits a 1+, 2+ topical response at 24 and 48 hours. The compound 4'-aminomethyl-4,5',8-trimethylpsoralen shows a high order of oral toxicity, a large number of the animals receiving 40 mgm/kgm thereof dying during the period of their observation, the LD50 for that particular compound apparently being much less than this dosage level.

It is to be understood that the invention is not to be limited to the exact details of operation or exact compounds, compositions, methods, or procedures shown and described, as obvious modifications and equivalents will be apparent to one skilled in the art.

I claim:

1. 5'-primaryaminoloweralkyl-4',4-diloweralkylpsoralen.

2. A compound of claim 1 which is 5'-aminomethyl-4',4-dimethylpsoralen.

3. The method of effecting photochemical sensitivity on the skin of a mammal comprising the step of orally or topically administering to the said mammal an effective photosensitizing dose of a compound of claim 1.

4. The method of claim 3 wherein the compound is 5'-aminomethyl-4',4-dimethylpsoralen.

5. A pharmaceutical composition suitable for use in effecting photochemical sensitivity on the skin of a mammal comprising a photosensitising effective amount of a compound of claim 1 and a pharmaceutical carrier therefor.

6. The composition of claim 5, wherein the compound is 5'-aminomethyl-4',4-dimethylpsoralen.

* * * * *

UNITED STATES PATENT AND TRADEMARK OFFICE
CERTIFICATE OF CORRECTION

PATENT NO. : 4,298,614

DATED : November 3, 1981

INVENTOR(S) : Kurt D. Kaufman

It is certified that error appears in the above—identified patent and that said Letters Patent is hereby corrected as shown below:

[56] References Cited, U.S. PATENT DOCUMENTS, line 2, third column (inventor); "Confalne et al." should read -- Confalone et al. -- copy of original Letters Patent No. 4,130,568.

[56] References Cited, U.S. PATENT DOCUMENTS, line 3, third column (inventor); "Heart et al." should read -- Hearst et al. -- copy of original Letters Patent No. 4,169,204.

Col. 1, line 58; "agents" should read -- agent --
Col. 3, line 64; "4 dimethylpsoralen" should read -- 4-dimethylpsoralen --
Col. 4, lines 51 & 52; "exchangable" should read -- exchangeable --
Col. 4, line 54; "$CH_8H$" should read -- $C_8H$ --
Col. 5, line 23; "113" should read -- 133 --
Col. 5, line 33; "exchangable" should read -- exchangeable --
Col. 6, line 63; "photosensitising" should read -- photosensitizing --

Attachment to Notice of Allowance and Base Issue Fee Due, paper Number 12, note amendment to Claims.

Signed and Sealed this

Second Day of March 1982

[SEAL]

Attest:

GERALD J. MOSSINGHOFF

Attesting Officer    Commissioner of Patents and Trademarks